(12) United States Patent
Ko et al.

(10) Patent No.: US 10,086,019 B1
(45) Date of Patent: Oct. 2, 2018

(54) **METHOD TO REDUCE INSULIN RESISTANCE AND IMPROVE GLUCOSE TOLERANCE USING *PARABACTEROIDES GOLDSTEINII***

(71) Applicant: Chang Gung Biotechnology Corp., Taipei (TW)

(72) Inventors: Yun-Fei Ko, Taipei (TW); Jan Martel, Taipei (TW); Tsung-Ru Wu, Taipei (TW); Chih-Jung Chang, Taipei (TW); Chuan-Sheng Lin, Taipei (TW); Jian-Ching Liau, Taipei (TW); Wei-Chang Wang, Taipei (TW); Chen-Yaw Chiu, Taipei (TW); Chia-Chen Lu, Taipei (TW); David Marcelo Ojcius, Taipei (TW); Hsin-Chih Lai, Taipei (TW); John D. Young, Taipei (TW)

(73) Assignee: CHANG GUNG BIOTECHNOLOGY CORP., Taipei (TW)

( * ) Notice: Subject to any disclaimer, the term of this patent is extended or adjusted under 35 U.S.C. 154(b) by 0 days.

(21) Appl. No.: 15/791,010

(22) Filed: Oct. 23, 2017

(30) Foreign Application Priority Data

Aug. 22, 2017 (TW) .............................. 106128476 A

(51) Int. Cl.
*A61K 49/00* (2006.01)
*A61K 48/00* (2006.01)
*A01N 63/00* (2006.01)
*A61K 35/74* (2015.01)
*A61K 9/00* (2006.01)

(52) U.S. Cl.
CPC ............ *A61K 35/74* (2013.01); *A61K 9/0053* (2013.01)

(58) Field of Classification Search
CPC .... A61K 35/00; A61K 35/741; A61K 35/742; A61K 35/744; A61K 39/00; A61K 9/02
USPC ................................ 424/9.1, 9.2, 93.1, 93.4
See application file for complete search history.

*Primary Examiner* — Rodney P Swartz

(74) *Attorney, Agent, or Firm* — WPAT, PC

(57) ABSTRACT

The present invention provides a method to reduce insulin resistance and improve glucose tolerance by administering the probiotic bacterium *Parabacteroides goldsteinii*. This probiotic bacterium can therefore be used to treat insulin resistance, metabolic syndrome, and type 2 diabetes.

9 Claims, 3 Drawing Sheets

METHOD TO REDUCE INSULIN RESISTANCE AND IMPROVE GLUCOSE TOLERANCE USING *PARABACTEROIDES GOLDSTEINII*

CROSS-REFERENCE TO RELATED APPLICATION

This application claims priority of Taiwan patent application No. 106128476, filed on Aug. 22, 2017, the content of which is incorporated herein in its entirety by reference.

BACKGROUND OF THE INVENTION

1. Field of the Invention

The present invention relates to a method to reduce insulin resistance and improve glucose tolerance. Particularly, the present invention provides a method to reduce insulin resistance and improve glucose tolerance by administering *Parabacteroides goldsteinii*.

2. The Prior Art

According to the World Health Organization, the global incidence of type 2 diabetes mellitus in adults has more than doubled since 1980 to reach worldwide epidemic status. In 2014, it was estimated that 8.5% (422 million) of the human population had type 2 diabetes. Diabetic individuals are at increased risk of developing blindness, kidney failure, hypertension, heart attacks and strokes, which may reduce quality of life and lead to premature death. Insulin resistance, a condition in which the cells of the body respond poorly to insulin, may occur prior to type 2 diabetes and lead to fatigue and various metabolic disorders (i.e., metabolic syndrome). While aging and genetic inheritance may be involved in the development of insulin resistance and diabetes, the diabetes epidemic has been mainly attributed to poor nutrition, smoking and lack of physical exercise. Type 2 diabetes and its complications may therefore be prevented by lifestyle changes.

Many pharmaceutical drugs have been approved for the treatment of type 2 diabetes, including biguanides, alpha-glucosidase inhibitors, glucagon-like peptides, meglitinides, sodium glucose transporter 2 inhibitors, sulfonylureas, and thiazolidinediones. Unfortunately, these drugs often produce side-effects which may reduce treatment efficacy and patient compliance. Low-calorie diets and regular exercise are part of the strategies used to treat diabetes, but these approaches are difficult to implement and their long-term efficacy has been disappointing. For these reasons, alternative strategies to treat type 2 diabetes in a safe and effective manner are highly needed.

The gut microbiota participates in various physiological functions, such as energy regulation, nutrient absorption, vitamin production, and toxin neutralization. Gut dysbiosis has been noted in diabetic patients, but it remains unclear whether probiotic bacteria may be used to treat insulin resistance and type 2 diabetes.

SUMMARY OF THE INVENTION

The present invention provides a method for reducing insulin resistance and improving glucose tolerance in a subject in need thereof, including administering a composition containing an effective amount of *Parabacteroides goldsteinii* bacterium to the subject.

In one embodiment of the present invention, *P. goldsteinii* bacterium is a live bacterium, and the composition is orally administered to the subject in need thereof. The effective amount of *P. goldsteinii* bacterium is between 0.001 colony-forming units (CFUs)/kg and $5 \times 10^{18}$ CFUs/kg of body weight per day. For a human subject (with an average body weight of 70 kg), the effective amount of *P. goldsteinii* bacterium is $6.1 \times 10^9$ CFUs per individual per day.

The composition containing *P. goldsteinii* may include an additional active ingredient, which is at least one selected from the group consisting of monosaccharides, disaccharides, oligosaccharides, polysaccharides, carbohydrates, amino acids, proteins, lipids, vitamins, and any combinations thereof. The composition containing *P. goldsteinii* may further include other bacteria species. For practical use, the composition containing *P. goldsteinii* may be in the form of a solution, a gelatin capsule, a softgel capsule, or a tablet.

The present invention discloses that *P. goldsteinii* in mammals effectively reduces insulin resistance and improves glucose tolerance. Therefore, *P. goldsteinii* can be used as a medication, a supplement, a food, or a drink for treatment of type 2 diabetes mellitus or metabolic syndrome.

The present invention is further explained in the following drawings and examples. It is understood that the examples given below do not, however, limit the scope of the invention, and it will be evident to those skilled in the art that modifications can be made without departing from the scope of the appended claims.

DETAILED DESCRIPTION OF THE PREFERRED EMBODIMENT

Definition

Figure 1:
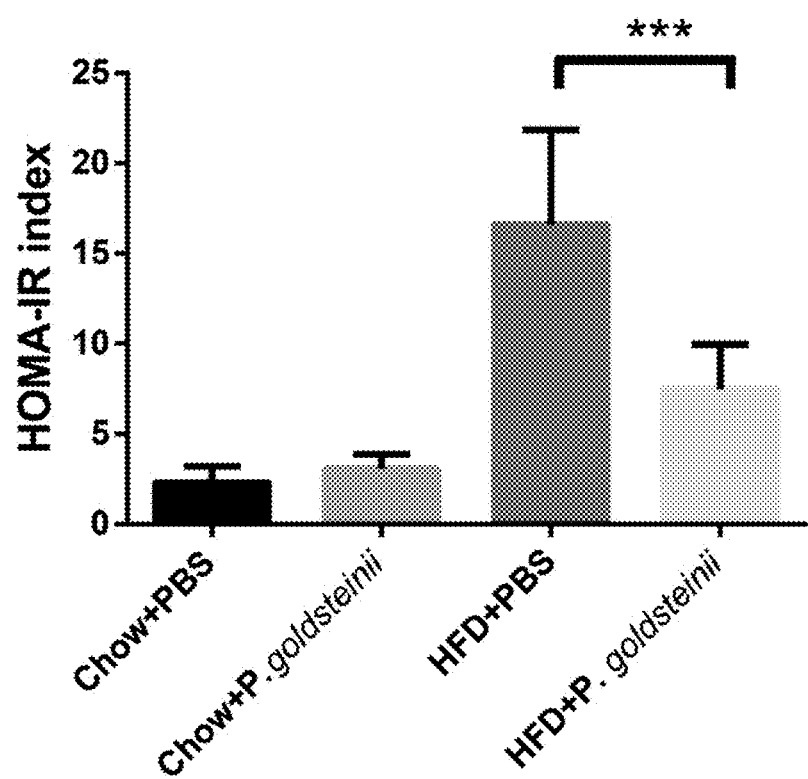
FIG. 1 shows the effects of *P. goldsteinii* on insulin resistance in mice fed with chow or high-fat diet (HFD). The homeostatic model assessment-insulin resistance (HOMA-IR) was used to monitor insulin resistance. For comparison, a group of mice was treated with phosphate-buffered saline (PBS) as a negative control; ***$P<0.001$.

As used herein, the term "effective amount" refers to the amount of bacteria that can reduce insulin resistance (HOMA-IR) and improve glucose tolerance in animals and humans The effective amount may vary depending on the organism or individual treated but can be determined experimentally using various techniques, including a dose escalation study.

The data provided in this specification represent approximated, experimental values that may vary within a range of ±20%, preferably ±10%, and most preferably ±5%.

The present invention provides a method to reduce insulin resistance and improve glucose tolerance by administering a composition containing an effective amount of *Parabacteroides goldsteinii* bacteria to a subject in need thereof. Therefore, *P. goldsteinii* may be used to treat type 2 diabetes and metabolic syndrome. The following experiments show that treating an insulin-resistant or type 2 diabetic subject with *P. goldsteinii* reduces insulin resistance and improves glucose tolerance. Generally, *P. goldsteinii* can be given to mammals and humans at a dose ranging from 0.001 CFUs/kg to $5 \times 10^{18}$ CFUs/kg of body weight per day. Details of the present invention are provided below.

Materials and Methods

Bacteria Culture

The bacteria used in the examples of the present invention, including *Parabacteroides goldsteinii* (ATCC strain BAA-1180) and *Parabacteroides merdae* (ATCC strain 43184), were purchased from the American Type Culture Collection (ATCC). The bacteria were cultured in liquid thioglycollate medium under anaerobic conditions containing 10% carbon dioxide, 10% hydrogen and 80% nitrogen at 37° C. (DG250 Anaerobic Workstation; Don Whitley Scientific, UK).

Homeostatic Model Assessment-Insulin Resistance (HOMA-IR) and Oral Glucose Tolerance Test (OGTT)

Fasting blood glucose was measured after six hours of fasting in mice using glucometer strips (Johnson & Johnson Medical Devices, HK). Commercial enzyme-linked immunosorbent assay (ELISA) kit was used to measure fasting insulin according to the manufacturer's instructions (Mercodia, Sweden). HOMA-IR index was determined using the following equation:

Fasting glucose (mg/dl)×fasting insulin (μU/ml)/405

To perform OGTT, eight-hour fasted mice were given a glucose solution (10%, w/v) by intragastric gavage at a dose of 1 g/kg and blood glucose was determined at a fixed interval.

Statistical Analysis

Data are presented as means ± standard deviation. Data were analyzed using one-way ANOVA followed by Bonferroni post hoc test.

EXAMPLE 1

Effects of *P. goldsteinii* Bacterium on Insulin Resistance and Glucose Tolerance in HFD-Fed Mice Eight-week old C57BL/6J male mice were fed with standard chow (13.5% of energy from fat; Laboratory Rodent Diet 5001; LabDiet, USA) or with HFD (60% of energy from fat; TestDiet 58Y1; TestDiet, USA). The mice were also treated daily with 200 μl of PBS containing *P. goldsteinii* ATCC strain BAA-1180 ($2 \times 10^6$ CFUs) or *P. merdae* ATCC strain 43184 ($2 \times 10^6$ CFUs), or with PBS alone for eight weeks by intragastric gavage (n=6 mice/group). Accordingly, these mice were assigned into groups denoted as Chow+PBS, Chow+*P. goldsteinii*, HFD+PBS, HFD+*P. goldsteinii*, and HFD+*P. merdae*. After eight weeks, each mouse group was subjected to HOMA-IR measurement and OGTT.

FIG. 1 shows the effects of *P. goldsteinii* on insulin resistance (HOMA-IR index) in chow-fed and HFD-fed mice. According to FIG. 1, feeding with HFD increased insulin resistance compared to feeding with chow. Notably, the mice treated with HFD+*P. goldsteinii* showed significant reduction of insulin resistance compared to the mice treated with HFD+PBS, indicating that treatment with *P. goldsteinii* significantly reduced insulin resistance in subjects in need.

Figure 2:
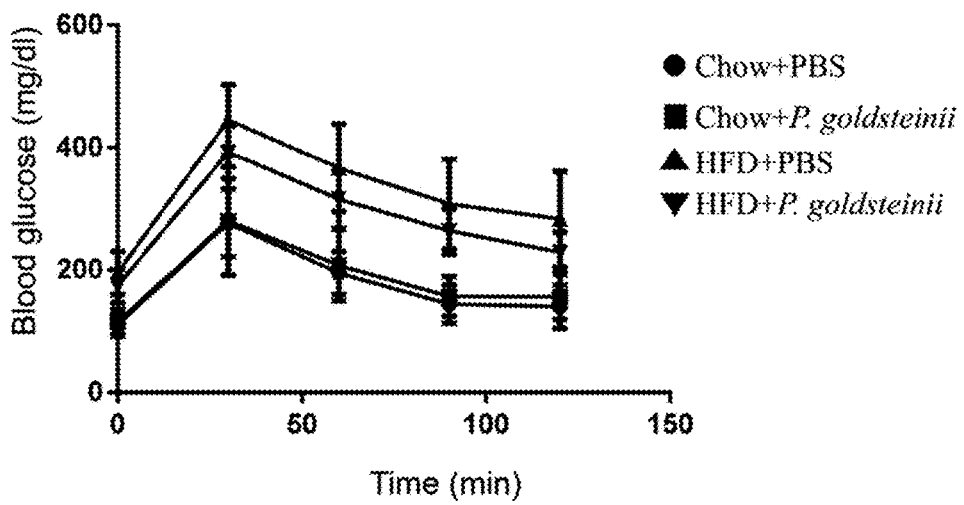
FIG. 2 shows the effects of *P. goldsteinii* on the oral glucose tolerance test (OGTT) in mice fed with chow or HFD.
Figure 3:
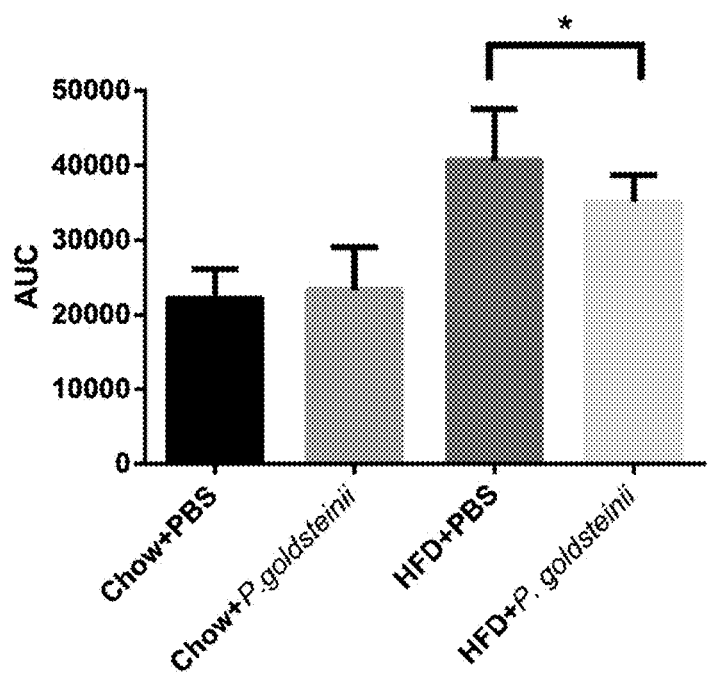
FIG. 3 shows the effects of *P. goldsteinii* on the OGTT in mice fed with chow or HFD. The results correspond to the area under the curve (AUC) of the data shown in FIG. 2. AUC values were calculated using the trapezoidal method and expressed as arbitrary units; *$P<0.05$.

FIG. 2 and FIG. 3 show the effects of *P. goldsteinii* on the OGTT in chow-fed and HFD-fed mice. According to FIG. 2 and FIG. 3, after a challenge with glucose, the concentration of glucose in the blood of HFD-fed mice was consistently higher than that in chow-fed mice. In comparison, supplementation with *P. goldsteinii* significantly reduced blood glucose concentration in HFD-fed mice, indicating that treatment with *P. goldsteinii* improved glucose tolerance in the treated subjects.

As shown in FIG. 1-3, *P. goldsteinii* can reduce insulin resistance and improve glucose tolerance in HFD-fed mice. Based on these results, the effective amount of *P. goldsteinii* required to produce insulin-sensitizing or anti-diabetic effects in mice (with an average body weight of 23 g) is $8.7 \times 10^7$ CFUs/kg of body weight per day (for a period of eight weeks). Accordingly, the effective amount of *P. goldsteinii* that would produce similar insulin-sensitizing effect in a human subject (with an average weight of 70 kg) is estimated at $6.1 \times 10^9$ CFUs/individual per day (for a period of eight weeks).

COMPARATIVE EXAMPLE

Figure 4:
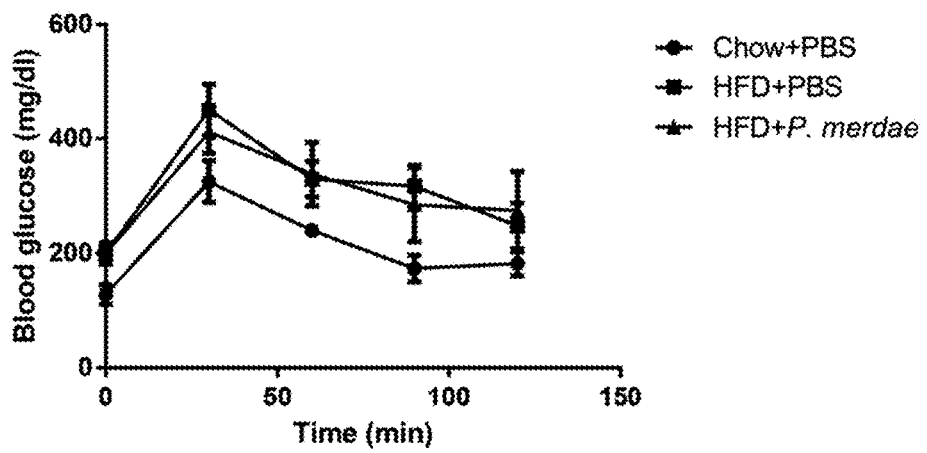
FIG. 4 shows the absence of effects of *Parabacteroides merdae* on the OGTT in mice fed with chow or HFD.
Figure 5:
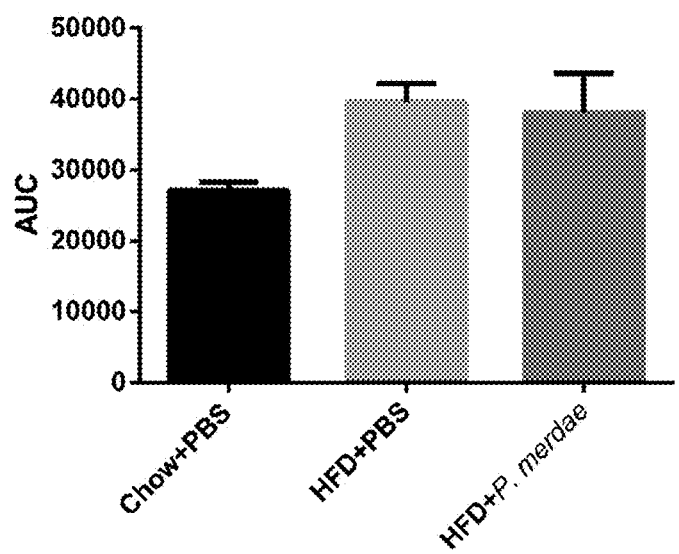
FIG. 5 shows the absence of effects of *P. merdae* on the OGTT in mice fed with chow or HFD. The results correspond to AUC values of the data presented in FIG. 4.

FIG. 4 and FIG. 5 show the effects of *P. merdae*, another member of the *Parabacteroides* genus which was used as a negative control, on the oral glucose tolerance test in chow-fed and HFD-fed mice. According to FIG. 4 and FIG. 5, eight weeks of HFD feeding and treatment with *P. merdae* (HFD+*P. merdae*) did not affect blood glucose compared with the HFD+PBS group. These results indicate that the insulin-sensitizing effect of *P. goldsteinii* is not a general characteristic of the *Parabacteroides* genus, but that it may be limited to *P. goldsteinii*.

EXAMPLE 2

Effects of *P. goldsteinii* Bacterium on Blood Biochemical Parameters in HFD-Fed Mice The effects of *P. goldsteinii* treatment on blood biochemical parameters in chow-fed mice were evaluated in this example. Hepatic functions were assessed by measuring the levels of aspartate transaminase (AST) and alanine transaminase (ALT), while renal functions were monitored by measuring blood urea nitrogen (BUN) and creatinine levels (TABLE 1). These blood biochemical parameters were monitored using a biochemical analyzer (Hitachi 7080, Hitachi, Japan). According to TABLE 1, no statistical differences were noted between the blood biochemical parameters of the Chow+PBS and Chow+*P. goldsteinii* groups, indicating that *P. goldsteinii* treatment did not affect liver or kidney functions.

TABLE 1

Analysis of hepatic and renal functions in mice treated with *P. goldsteinii*

|  | Chow + PBS | Chow + *P. goldsteinii* |
|---|---|---|
| Aspartate transaminase (AST; U/l) | 73.9 ± 13.4 | 72.4 ± 19.9 |
| Alanine transaminase (ALT; U/l) | 30.4 ± 11.2 | 26.3 ± 4.8 |
| Blood urea nitrogen (BUN; mg/dl) | 29.8 ± 3.8 | 28.3 ± 2.8 |
| Creatinine (mg/dl) | 0.20 ± 0.05 | 0.20 ± 0.04 |

Data in TABLE 1 were based on triplicate experiments (n=14-16 mice per group).

The experiments described above show that treatment with *P. goldsteinii* can effectively reduce insulin resistance and improve glucose tolerance in mammals, and thus *P. goldsteinii* may be used to treat insulin resistance, type 2 diabetes, and metabolic syndrome. However, not all bacterial species of the *Parabacteroides* genus are capable of reducing insulin resistance and improving glucose tolerance, as shown by the lack of effectiveness of *P. merdae* in the comparative example. *P. goldsteinii* can be added to the diet of a subject, as a medication, a supplement, a food, or a drink, without incurring in significant lifestyle changes, toxicity or other unfavorable health conditions. Therefore, the present invention provides a new strategy to treat insulin resistance, type 2 diabetes, and metabolic syndrome. The present invention has obvious commercial value in view of the pressing need in the market for products that can be used to prevent or treat insulin resistance, type 2 diabetes and metabolic syndrome.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for reducing insulin resistance and improving glucose tolerance in a subject on a high fat diet, comprising administering a composition containing an effective amount of *Parabacteroides goldsteinii* bacterium to the subject for at least eight weeks.

2. The method of claim 1, wherein the composition is orally administered to the subject.

3. The method of claim 1, wherein the *Parabacteroides goldsteinii* bacterium is a live bacterium.

4. The method of claim 1, wherein the effective amount of the *Parabacteroides goldsteinii* bacterium is between 0.001 CFUs/kg and $5\times10^{18}$ CFUs/kg of body weight per day.

5. The method of claim 1, wherein the effective amount of the *Parabacteroides goldsteinii* bacterium is $6.1\times10^9$ CFUs per day.

6. The method of claim 1, wherein the composition further comprises an additional active ingredient.

7. The method of claim 6, wherein the additional active ingredient is at least one selected from the group consisting of monosaccharide, disaccharide, oligosaccharide, polysaccharide, carbohydrate, amino acid, protein, lipid, vitamin, and any combination thereof.

8. The method of claim 1, wherein the composition further comprises other bacteria species.

9. The method of claim 1, wherein the composition is in the form of a solution, a gelatin capsule, a softgel capsule, or a tablet.

\* \* \* \* \*